United States Patent [19]

Sakamoto et al.

[11] 4,342,693
[45] Aug. 3, 1982

[54] 1,3-DIOXOLEN-2-ONE DERIVATIVES AND PROCESS FOR PRODUCTION THEREOF

[75] Inventors: Fumio Sakamoto, Osaka; Shoji Ikeda, Ibaraki; Goro Tsukamoto, Toyonaka; Isamu Utsumi, Kyoto, all of Japan

[73] Assignee: Kanebo Ltd., Tokyo, Japan

[21] Appl. No.: 257,564

[22] Filed: Apr. 27, 1981

[30] Foreign Application Priority Data

Apr. 30, 1980 [JP] Japan ................................. 55-58510

[51] Int. Cl.³ .................. C07D 317/46; C07D 317/40
[52] U.S. Cl. .................................. 549/229; 260/239.1
[58] Field of Search ...................................... 260/340.2

[56] References Cited

U.S. PATENT DOCUMENTS 3,020,290 2/1962 Moss ................................. 260/340.2

OTHER PUBLICATIONS

H. D. Scharf et al, Liebigs *Ann. Chem.* (1977) pp. 27-32.
Herbert O. House, *Modern Synthetic Reactions*, 2nd ed. (1971) pp. 478-487.
*Liebigs Annalen der Chemie*, vol. 764, pp. 116-124 (1972).
*Tetrahedron Letters*, No. 17, pp. 1701-1704 (1972).
*Bulletin of the Chemical Society of Japan*, vol. 45, pp. 2797-2801 (1972).
*Transactions, Ill. State Acad. Sci.*, vol. 67, No. 1, pp. 139-145 (1974).

*Primary Examiner*—Norma S. Milestone
*Attorney, Agent, or Firm*—Wenderoth, Lind & Ponack

[57] ABSTRACT

A 1,3-dioxolen-2-one derivative of the general formula

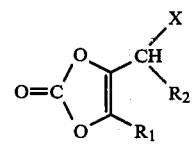

wherein $R_1$ represents a hydrogen atom, a methyl group, or an aryl group, $R_2$ represents a hydrogen atom, or may be taken together with $R_1$ to form a divalent carbon chain residue, and x represents a halogen atom.

The above compounds can be prepared by reacting a compound of the general formula

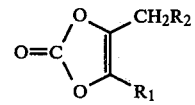

with a halogenating agent, and are useful as protective group-introducing reagents for introducing protective groups into reagents in various chemical reactions, or as modifiers for prodrug preparation in medicine.

14 Claims, No Drawings

1,3-DIOXOLEN-2-ONE DERIVATIVES AND PROCESS FOR PRODUCTION THEREOF

This invention relates to novel 1,3-dioxolen-2-one derivatives and a process for production thereof. More specifically, it relates to novel 1,3-dioxolen-2-one derivatives which are useful as protective group-introducing reagents for introducing protective groups into reagents in various chemical reactions, or as modifiers for pro-drug preparation in medicine, and to a process for production thereof.

In various chemical reactions, it is frequently the practice to protect a certain number of reactive sites of a reagent so as to induce the desired reaction and eliminate the protective groups after the reaction. For example, in acylating the amino group of an amino acid, the carboxyl group is protected in advance with a protective group, and after the acylation of the amino group, the protective group is removed to obtain an N-acylamino acid.

Some pharmaceuticals, despite their high pharmacological activity, cannot sufficiently exhibit their pharmaceutical utility because of their chemical instability or poor bioavailability. One method for remedying such a defect is to convert a pharmaceutical into a prodrug by chemically modifying it. For example, a pharmaceutical having low intestinal absorption is chemically modified in part to increase its intestinal absorption. When administered to a living organism, this modified pharmaceutical undergoes chemical and biological actions within the organism and reverts to the parent pharmaceutical, thereby exhibiting its inherent pharmacological activity.

It is an object of this invention to provide novel 1,3-dioxolen-2-one derivatives.

Another object of this invention is to provide novel 1,3-dioxolen-2-one derivatives which can be used as protective group-introducing agents in various chemical reactions.

Still another object of this invention is to provide novel 1,3-dioxolen-2-one derivatives which can be used as modifiers for various pharmaceuticals and therefore give prodrugs having improved bioavailability over the parent pharmaceuticals.

A further object of this invention is to provide a process for producing novel 1,3-dioxolen-2-one derivatives.

Other objects and advantages of this invention will become apparent from the following description.

In accordance with this invention, these objects and advantages are achieved by a 1,3-dioxolen-2-one derivative of the general formula

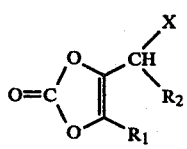

(I)

wherein $R_1$ represents a hydrogen atom, a methyl group or an aryl group, $R_2$ represents a hydrogen atom or may be taken together with $R_1$ to form a divalent carbon chain residue, and X represents a halogen atom.

The present invention also provides a process for producing a 1,3-dioxolen-2-one derivative of the general formula

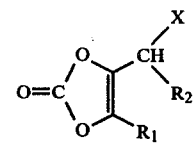

(I)

wherein $R_1$ represents a hydrogen atom, a methyl group or an aryl group, $R_2$ represents a hydrogen atom or may be taken together with $R_1$ to form a divalent carbon chain residue, and X represents a halogen atom, which comprises reacting a compound of the general formula

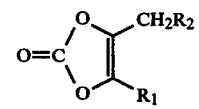

(II)

wherein $R_1$ and $R_2$ are as defined above, with a halogenating agent.

The 1,3-dioxolen-2-one derivative provided by this invention is expressed by the following general formula

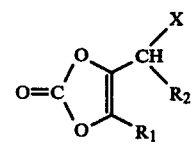

(I)

wherein $R_1$ represents a hydrogen atom, a methyl group or an aryl group, $R_2$ represents a hydrogen atom or may be taken together with $R_1$ to form a divalent carbon chain residue, and X represents a halogen atom.

In formula (I), $R_1$ represents a hydrogen atom, a methyl group or an aryl group. The aryl group is preferably an aromatic hydrocarbon group such as phenyl and substituted phenyl groups, and the phenyl group is especially preferred. The substituted phenyl groups may have such a substituent as a halogen atom, a nitro group, and a lower alkoxy group. Thus, $R_1$ is preferably a hydrogen atom, a methyl group, or a phenyl group.

$R_2$ is a hydrogen atom, or together with $R_1$, may form a divalent carbon chain residue. When $R_2$ and $R_1$ together form a divalent carbon chain residue, $R_1$, $R_2$, and the group C=C—CH to which $R_1$ and $R_2$ are bonded form a ring. Preferably, the divalent carbon chain residue is such that the aforesaid ring is 5- to 8-membered, especially 6- or 8-membered. Examples of preferred divalent carbon chain residue are $-(CH_2)_3-$ and $-(CH_2)_5-$.

X is a halogen atom such as chlorine, bromine and iodine, and bromine and chlorine are preferred.

The 1,3-dioxolen-2-one derivative of general formula (I) reacts, for example, with carboxylic acids, thiocarboxylic acids or phenols to give the corresponding carboxylates, thiocarboxylates or ethers. In such reactions, the 1,3-dioxolen-2-one derivative liberates the halogen atom X and reacts with the carboxylic acids, etc. to give the corresponding carboxylates, etc. Accordingly, the 1,3-dioxolen-2-one derivative of this invention gives the same reaction products in the aforesaid reactions involving liberation of X irrespective of the type of X, e.g. irrespective of whether X is chlorine or bromine.

Preferred 1,3-dioxolen-2-one derivatives of this invention are those of general formula (I) in which $R_1$ is a methyl group and $R_2$ is a hydrogen atom, $R_1$ and $R_2$ are both hydrogen atoms, $R_1$ is a phenyl group and $R_2$ is a hydrogen atom, and $R_1$ and $R_2$ together form the group -(-CH$_2$-)$_3$ or -(-CH$_2$-)$_5$.

Specific examples of the compound of general formula (I) are
4-chloromethyl-1,3-dioxolen-2-one,
4-bromomethyl-1,3-dioxolen-2-one,
4-chloromethyl-5-phenyl-1,3-dioxolen-2-one,
4-bromomethyl-5-phenyl-1,3-dioxolen-2-one,
4-chloromethyl-5-methyl-1,3-dioxolen-2-one,
4-bromomethyl-5-methyl-1,3-dioxolen-2-one,
4-iodomethyl-5-methyl-1,3-dioxolen-2-one,
3-chloro-1,2-carbonyldioxycyclohexene,
3-bromo-1,2-carbonyldioxycyclohexene,
3-chloro-1,2-carbonyldioxycyclooctene, and
3-bromo-1,2-carbonyldioxycyclooctene.

According to the process of this invention, the 1,3-dioxolen-2-one derivative of general formula (I) can be produced by reacting a compound of the general formula

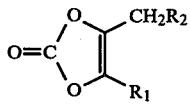
(II)

wherein $R_1$ and $R_2$ are as defined above, with a halogenating agent.

Among the compounds of general formula (II), 4-methyl-5-phenyl-1,3-dioxolen-2-one, 4,5-dimethyl-1,3-dioxolen-2-one, etc. are known from Liebigs Annalen der Chemie, Vol. 764, pages 116–124 (1972), Tetrahedron Letters, pages 1701–1704, 1972, or U.S. Patent No. 3,020,290. The compounds of general formula (II) can be produced by the methods described in these known publications. Accordingly, in the present specification, these publications are cited as references.

Examples of the compounds of general formula (II) include 4-methyl-1,3-dioxolen-2-one, 4-methyl-5-phenyl-1,3-dioxolen-2-one, 4,5-dimethyl-1,3-dioxolen-2-one, 1,2-carbonyldioxycyclohexene, and 1,2-carbonyldioxycyclooctene.

The process of the invention is carried out by reacting the compound of general formula (II) with a halogenating agent. The halogenating agent is preferably an allylic halogenating agent. Examples of preferred allylic halogenating agents are N-bromosuccinimide, N-chlorosuccinimide, N-bromophthalimide, N-chlorophthalimide, bromine, chlorine and t-butylhypoiodide. According to the above process of the invention, compounds of general formula (I) in which X is chlorine or bromine can be conveniently produced.

In the reaction, the halogenating agent is used in an amount of at least 1 mole per mole of the compound of general formula (II). The reaction is carried out generally in an aprotic inert organic solvent. The solvent is preferably a hydrocarbon or halogenated hydrocarbon which is liquid under the reaction conditions. Examples of preferred solvents are methylene chloride, chloroform, carbon tetrachloride, tetrachloroethylene, benzene and chlorobenzene. The solvent is properly selected depending upon the properties of the compounds of formula (II) and the halogenating agent.

The reaction proceeds at room temperature to the refluxing temperature of the reaction system. It is believed that the reaction is a radical reaction. The reaction favorably proceeds by causing a radical generator to be present in the reaction system, and/or by irradiating ultraviolet light to the reaction system.

The radical generator may be a known radical generator such as $\alpha,\alpha'$-azobisisobutyronitrile or benzoyl peroxide.

The reaction under preferred reaction conditions proceeds to a favorable extent within several minutes to several hours.

After the reaction, the reaction mixture is concentrated, and any insoluble material is removed by filtration. The filtrate is concentrated to obtain a crude product. Recrystallization or distillation of the crude product gives a purified product.

Compounds of general formula (I) in which X is iodine can be produced by subjecting the corresponding 1,3-dioxolen-2-one derivatives of general formula (I) wherein X is chlorine or bromine, which can be conveniently produced by the method described above, to a known halogen-substitution reaction such as reaction with a metal iodide.

The novel 1,3-dioxolen-2-one derivatives provided by the present invention can be used, for example, as protective group-introducing reagents in various chemical reactions, or as modifiers for pharmaceuticals.

A carboxylate obtained by reacting the 1,3-dioxolen-2-one derivative of the invention with a carboxylic acid or an ether obtained by reacting it with a phenol is stable in neutral and acidic media but is susceptible to hydrolysis in alkaline aqueous media or in the presence of a suitable enzyme. Accordingly, an amino acid can be acylated, for example, by reacting the amino acid with the 1,3-dioxolen-2-one derivative of the invention in an aprotic inert solvent in the presence of a base to esterify its carboxyl group, then acylating the amino group, and hydrolyzing the ester group of the product in alkalinity.

An ester obtained by reacting the 1,3-dioxolen-2-one derivative of the invention with a carboxylic acid readily undergoes hydrolysis in an ordinary alkaline aqueous medium as stated above. But when the ester is administered orally, it is relatively stable in the alkaline intestinal fluid and easily undergoes hydrolysis in the presence of enzymes to be converted back to the parent carboxylic acid. This property demonstrates that the 1,3-dioxolen-2-one derivative of the invention is suitable for converting a pharmaceutical having low bioavailability into a prodrug having increased bioavailability.

The following Examples and Referential Examples illustrate the present invention more specifically.

EXAMPLE 1

Production of 4-bromomethyl-5-phenyl-1,3-dioxolen-2-one:

In 150 ml of carbon tetrachloride was dissolved 2.4 g of 4-methyl-5-phenyl-1,3-dioxolen-2-one (synthesized by the method described in Liebigs Annalen der Chemie, Vol. 764, pages 116–124, 1972). N-bromosuccinimide (2.9 g) and a catalytic amount of $\alpha,\alpha'$-azobisisobutyronitrile were added to the solution, and the mixture was heated under reflux for 90 minutes. The reaction mixture was concentrated to one half of its volume, and the insoluble material was separated by filtration. The filtrate was concentrated, and the residue was recrystallized from a mixture of benzene and cyclohexane to give 2.3 g (yield 66%) of colorless needles having a melting point of 90.5° to 91.5° C. This product had the following properties.

Elemental analysis, molecular formula $C_{10}H_7BrO_3$:
Calculated (%): C, 47.09; H, 2.77; Br, 31.33; Found (%): C, 47.22; H, 2.64; Br, 31.29.
IR (KBr): near 1825 cm$^{-1}$ ($\nu_{c=o}$)
NMR (CCl$_4$, δ(ppm)):
4.35 (C—CH$_2$Br, s), 7.40 (benzene ring, s).

From these data, the product was identified as the title compound.

EXAMPLE 2

Production of 4-bromomethyl-5-methyl-1,3-dioxolen-2-one:

In 150 ml of carbon tetrachloride was dissolved 3.42 g of 4,5-dimethyl-1,3-dioxolen-2-one (synthesized by the method described in Tetrahedron Letters, 1972, pages 1701-1704). N-bromosuccinimide (5.34 g) and a catalytic amount of α,α'-azobisisobutyronitrile were added to the solution, and the mixture was heated under reflux for 15 minutes. The reaction mixture was concentrated to one half of its volume, and the insoluble material was removed by filtration. The filtrate was concentrated, and the syrupy residue was distilled under reduced pressure to give 4.2 g (yield 73%) of a colorless liquid having a boiling point of 115°-120° C./5 mm. The product had the following properties.

Elemental analysis, molecular formula $C_5H_5BrO_3$:
Calculated (%): C, 31.12; H, 2.61; Br, 41.40; Found (%): C, 31.30; H, 2.49; Br, 41.31.
IR (neat): near 1825 cm$^{-1}$ ($\nu_{c=o}$) NMR (CCl$_4$, δ(ppm)): 2.10 (—CH$_3$, s), 4.10 (—CH$_2$Br, s).

From these data, the product was identified as the title compound.

EXAMPLE 3

Production of 4-bromomethyl-1,3-dioxolen-2-one:

In 200 ml of carbon tetrachloride was dissolved 8.6 g of 4-methyl-1,3-dioxolen-2-one (synthesized by the method described in U.S. Pat. No. 3,020,290). N-bromosuccinimide (17.8 g) and a catalytic amount of α,α'-azobisisobutyronitrile were added to the solution, and the mixture was heated under reflux for 90 minutes. The reaction mixture was worked up in the same way as in Example 2 to give 5.2 g (yield 33.6%) of a colorless liquid having a boiling point of 94° C./3 mm. The product had the following properties.

Elemental analysis, molecular formula $C_4H_3BrO_3$:
Calculated (%): C, 26.84; H, 1.69; Br, 44.65; Found (%): C, 26.94; H, 1.66; Br, 44.60.
IR (neat): 1830 cm$^{-1}$ ($\nu_{c=o}$) NMR (CCl$_4$, δ(ppm)): 4.10 (—CH$_2$Br, s), 7.00 (=CH—O—, s).

From these data, the product was identified as the title compound.

EXAMPLE 4

Production of 3-bromo-1,2-carbonyldioxycyclohexene:

In 80 ml of carbon tetrachloride was dissolved 2.15 g of 1,2-carbonyldioxycyclohexene (synthesized by the method described in Tetrahedron Letters, 1972, pages 1701-1704). N-bromosuccimide (2.3 g) and a catalytic amount of α,α'-azobisisobutyronitrile were added to the solution, and the mixture was heated under reflux for 20 minutes. The reaction mixture was cooled, and filtered. The filtrate was concentrated at a low temperature to give 3.2 g of a pale brown liquid as a residue. The product showed the following properties.

IR (neat): near 1825 cm$^{-1}$ ($\nu_{c=o}$) NMR (CDCl$_3$, δ(ppm)):
5.0

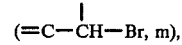
(=C—CH—Br, m), 1.3-3.0 (cyclic proton, m)

From these data, the product was identified as the title compound.

The product was unstable. Accordingly, without isolation and purification, it was reacted with Ampicillin to give Ampicillin ester (see Referential Example 2 below).

REFERENTIAL EXAMPLE 1

Ampicillin trihydrate (500 mg) was dispersed in 6 ml of dimethyl formamide, and 125 mg of potassium bicarbonate was added. The mixture was cooled to 0° C., and 0.25 ml of benzaldehyde was added. The mixture was stirred at 0° C. for 2.5 hours. Then, 125 mg of potassium bicarbonate and 250 mg of 4-bromomethyl-5-methyl-1,3-dioxolen-2-one (the product obtained in Example 2) were added, and the mixture was stirred at 0° C. for 3 hours. After the reaction, the reaction mixture was poured into ice water. The precipitated solid was extracted with 30 ml of ethyl acetate. The organic layer was washed with 20 ml of water three times, and dried over anhydrous magnesium sulfate. The ethyl acetate was distilled off under reduced pressure to give a yellow syrup.

The resulting syrupy residue was dissolved in 4 ml of acetonitrile and the solution was adjusted to pH 2.0 with dilute hydrochloric acid. The solution was then stirred at 0° C. for 30 minutes. Water (10 ml) was added, and the acetonitrile was distilled off under reduced pressure. The aqueous layer was washed repeatedly with ethyl acetate, and then saturated with sodium chloride. The separated oily substance was extracted with 50 ml of methylene chloride, and washed with a saturated aqueous solution of sodium chloride. The methylene chloride layer was dried over anhydrous sodium sulfate, filtered and concentrated under reduced pressure to one half of its volume. To the solution isopropyl alcohol (30 ml) was added, and the mixture was again concentrated under reduced pressure to give a colorless solid.

The solid was collected by filtration and washed with isopropyl alcohol and ether to give 312 mg (yield 50.6%) of Ampicillin (5-methyl-2-oxo-1,3-dioxolen-4-yl)methyl ester hydrochloride as a colorless amorphous solid. The product had the following properties.

Appearance: Colorless amorphous solid Melting point: 145° C. (decomp.)
Elemental analysis, molecular formula $C_{21}H_{23}N_3O_7S.HCl.H_2O$: Calculated (%): C, 48.88; H, 5.08; N, 8.14; S, 6.21. Found (%): C, 48.51; H, 5.15; N, 8.02; S, 6.44.
IR (KBr):
1825, 1785, 1750 cm$^{-1}$ ($\nu_{c=o}$), 1690 cm$^{-1}$ ($\nu_{CONH}$).

The resulting Ampicillin ester hydrochloride was incubated in 40% mouse blood in pH 7.4 phosphate buffer at 37° C. for 10 minutes, and then subjected to bioautography. It was found to be completely converted to Ampicillin.

REFERENTIAL EXAMPLE 2

In the same way as in Referential Example 1, Ampicillin (2,3-carbonyldioxy-2-cyclohexenyl) ester hydrochloride was obtained in a yield of 10.2% from Ampicillin trihydrate and 3-bromo-1,2-carbonyldioxycyclohexene. This product had the following properties.

Appearance: Colorless amorphous solid Melting point: 140° C. (decomp.)

IR (KBr): 1830, 1780, 1750 cm$^{-1}$ ($\nu_{c=o}$), 1690 cm$^{-1}$ ($\nu$CONH)

The resulting Ampicillin ester hydrochloride was incubated in the same way as in Referential Example 1 and was found to be completely converted to Ampicillin.

REFERENTIAL EXAMPLE 3

In the same way as in Referential Example 1, Ampicillin (5-phenyl-2-oxo-1,3-dioxolen-4-yl)methyl ester hydrochloride was obtained in a yield of 46.4% from Ampicillin trihydrate and 4-bromomethyl-5-phenyl-1,3-dioxolen-2-one. This product had the following properties.

Appearance: Colorless amorphous solid Melting point: 140° C. (decomp.)

Elemental analysis, molecular formula $C_{26}H_{25}N_3O_7S \cdot HCl \cdot 2H_2O$: Calculated (%): C, 52.39; H, 5.07; N, 7.05; S, 5.38.

Found (%): C, 52.17; H, 4.83; N, 7.31; S, 5.64.

IR (KBr):
1830, 1785, 1760 cm$^{-1}$ ($\nu_{c=o}$), 1690 cm$^{-1}$ ($\nu_{CONH}$).

The resulting Ampicillin (5-phenyl-2-oxo-1,3-dioxolen-4-yl)methyl ester hydrochloride was incubated in the same way as in Referential Example 1 and was found to be completely converted to Ampicillin.

REFERENTIAL EXAMPLE 4

In this example, the properties in vitro and in vivo of the Ampicillin ester produced in Referential Example 1 using the novel compound of this invention were compared with those of known Ampicillin phthalidyl ester hydrochloride and Ampicillin trihydrate. The results of this Referential Example 4 show the novel compounds of this invention to be useful as a modifier for prodrug preparation.

(1) [Concentration in blood in oral administration]
1. Test Compounds
   A. Ampicillin (5-methyl-2-oxo-1,3-dioxolen-4-yl)methyl ester hydrochloride.
   B. Ampicillin phthalidyl ester hydrochloride (known Ampicillin ester used as a control; see British Pat. No. 1,364,672)
   C. Ampicillin trihydrate (control)
2. Testing method Each of the test compounds was orally administered in a dose of 50.0 mg/kg calculated as Ampicillin to four week old mice (ddy, body weight about 20 g; five per group) which had been caused to fast overnight. Blood was periodically taken from the test animals, and the Ampicillin concentration in the serum was measured by a bioassay method. The ratio of the serum Ampicillin levels of the test compounds was calculated.
3. Results

TABLE 1

| Test compound | Item Serum Ampicillin level ratio Time of blood taking (min.) | | | | | |
|---|---|---|---|---|---|---|
| | 15 | 30 | 60 | 90 | 120 | 180 |
| A | 2.8 | 2.9 | 2.1 | 1.8 | 1.5 | 1.3 |
| B | 3.0 | 1.8 | 1.4 | 1.1 | 0.9 | 0.8 |
| C | 1 | 1 | 1 | 1 | 1 | 1 |

While the Ampicillin ester (A) derived from the compound of this invention is easily absorbed and converted back to the parent Ampicillin in vivo, the results given in Table 1 show that (A) shows higher blood concentrations of Ampicillin over longer periods of time than (B) and (C).

2. [Hydrolysis in an acidic medium (simulated gastric juice)]
   1. Test compounds A and B mentioned in (1) above.
   2. Testing method Each of the test compounds was dissolved in an acidic medium (pH 1.2) prepared by mixing 1000 ml of water with 2.0 g of sodium chloride, 24 ml of 10% hydrochloric acid and 3.2 g of pepsin. The solution was shaken at 37° C., and periodically sampled. The hydrolysis ratio of each compound was determined from a decrease in the peak height of each compound using a high-speed liquid chromatographic method (a reversed phase partition column).
3. Results

TABLE 2

| Test compound | Item Hydrolysis ratio (%) in an acidic medium Time of sampling (hours) | | | | |
|---|---|---|---|---|---|
| | 1 | 2 | 4 | 6 | 20 |
| A | 7 | 15 | 20 | 28 | 52 |
| B | 18 | 31 | 43 | 55 | 100 |

Table 2 shows that in the acidic medium, the Ampicillin ester (A) derived from the compound of the invention is much more stable than the known Ampicillin ester (B).

(3) [Hydrolysis in a basic medium (simulated intestinal juice)]
   1. Test compounds A and B mentioned in (1).
   2. Testing method Each of the test compounds was dissolved in a basic medium (pH 7.5) prepared by mixing 1000 ml of water with 35.8 g of disodium phosphate, 6.0 ml of 10% hydrochloric acid and 2.8 g of pancreatin. The hydrolysis ratio of each of the test compounds was determined in the same way as in (2) above.
3. Results

TABLE 3

| Test compound | Item Hydrolysis ratio (%) in a basic medium Time of sampling (min.) | | | | |
|---|---|---|---|---|---|
| | 5 | 10 | 20 | 30 | 60 |
| A | 16 | 32 | 48 | 65 | 80 |
| B | 39 | 61 | 90 | 95 | 100 |

Table 3 shows that the Ampicillin ester (A) derived from the compounds of this invention is more stable than the known Ampicillin ester (B).

(4) [Toxicity]

The toxicity (LD$_{50}$) of the compound (A) administered as an aqueous solution was examined using mice (four week old; ddy) to give the following results.

Oral administration: >5,000 mg/kg
Intraperitoneal administration: 1,430 mg/kg
Intravenous administration: 557 mg/kg.

It is seen from the foregoing that the 1,3-dioxolen-2-one derivatives of the invention are very useful as modifiers for prodrug preparation, and have very low toxicity. This utility cannot be anticipated at all from the prior knowledge.

REFERENTIAL EXAMPLE 5

(1) Production of 6-aminopenicillanic acid (5-methyl-2-oxo-1,3-dioxolen-4-yl)methyl ester p-toluenesulfonate-melting point 125°-135° C. (decomp.)

In 100 ml of dimethyl formamide was dissolved 13 g of 6-tritylaminopenicillanic acid synthesized by the method described in J. Am. Chem. Soc. 84, 2983 (1963). The solution was cooled to 0° to 5° C., and 3 g of potassium hydrogen carbonate and 6 g of 4-bromomethyl-5-methyl-1,3-dioxolen-2-one were added. The mixture was stirred at the above temperature for 3 hours. After the reaction, the reaction mixture was poured into ice water. The precipitated yellow solid was extracted with 300 ml of ethyl acetate. The ethyl acetate layer was washed several times with a saturated aqueous solution of sodium chloride, dried over anhydrous magnesium sulfate and concentrated under reduced pressure to give a yellow syrup. The syrup was dissolved in 80 ml of ethyl acetate, and with ice cooling, 5.2 g of p-toluenesulfonic acid was added. The mixture was stirred under ice cooling for 1 hour, whereupon a colorless solid precipitated. The solid was collected by filtration and well washed with ethyl acetate to give 8.3 g (yield 60%) of the title compound.

IR(KBr): 1820 cm$^{-1}$ (cyclic carbonate), 1780 cm$^{-1}$ ($\beta$-lactam), 1760 cm$^{-1}$ (ester).

NMR(DMSO-d$_6$, $\delta$(ppm)): 1.40 and 1.59 (6H, methyl at the 2-position, s),

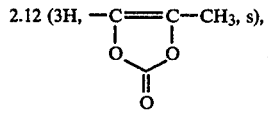

2.12 (3H, —C=C—CH$_3$, s), 4.46 (1H, proton at the 3-position, s),
4.90-5.10 (3H, proton at 6-position and

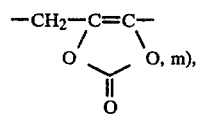

—CH$_2$—C=C—, m), 5.41 (1H, proton at the 5-position, d),

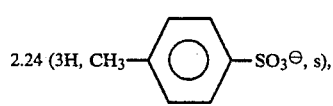

2.24 (3H, CH$_3$—⟨○⟩—SO$_3^\ominus$, s), 6.97 and 7.38 (4H, aromatic protons of

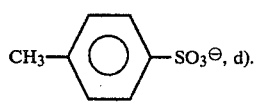

CH$_3$—⟨○⟩—SO$_3^\ominus$, d).

(2) Production of benzylpenicillin (5-methyl-2-oxo-1,3-dioxolen-4-yl)methyl ester 7.5 Grams of 6-aminopenicillanic acid (5-methyl-2-oxo-1,3-dioxolen-4-yl)methyl ester p-toluenesulfonate were suspended in 300 ml of ethyl acetate. To the suspension was added at 0° C. 200 ml of a 2% aqueous solution of sodium hydrogen carbonate cooled with ice. The mixture was vigorously stirred. The ethyl acetate layer was separated, washed with ice water, dried at 0° C. over anhydrous magnesium sulfate, and concentrated under reduced pressure to give a pale yellow syrup. The syrup was dissolved in 70 ml of methylene chloride. The solution was cooled to 0° C., and 1.5 g of sodium hydrogen carbonate and 4 g of phenylacetyl chloride were added, and the mixture was stirred at 0° C. for 5 hrs. Insoluble material was separated by filtration after the reaction, and the filtrate was washed with ice water, dried over anhydrous sodium sulfate, and concentrated under reduced pressure to give 5.9 g of benzylpenicillin (5-methyl-2-oxo-1,3-dioxolen-4-yl)methyl ester as pale yellow amorphous solid (Yield 87%).

IR(KBr): 1825 cm$^{-1}$ (cyclic carbonate), 1785 cm$^{-1}$ ($\beta$-lactam), 1750 cm$^{-1}$ (ester), 1670 cm$^{-1}$ (amide).

NMR(CDCl$_3$, $\delta$(ppm)): 1.37 and 1.42 (6H, methyl at the 2-position, s),

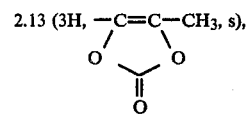

2.13 (3H, —C=C—CH$_3$, s),

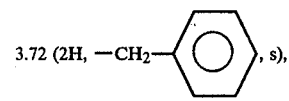

3.72 (2H, —CH$_2$—⟨○⟩, s), 4.29 (1H, proton at the 3-position, s),

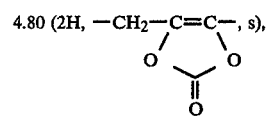

4.80 (2H, —CH$_2$—C=C—, s), 5.36 (1H, proton at the 6-position, m), 5.59 (1H, proton at the 5-position, d), 6.16 (1H, —CONH—, d), 7.14 (5H, aromatic protons, s).

(3) Production of benzylpenicillin

Fifty milligrams of benzylpenicillin (5-methyl-2-oxo-1,3-dioxolen-4-yl)methyl ester were suspended in a 20% mouse serum diluted with pH 7.4 phosphate buffer and incubated at 37° C. for 2 hours and then subjected to bioautography. It was found to be completely converted to benzylpenicillin.

What we claim is:

1. A 1,3-dioxolen-2-one derivative of the general formula

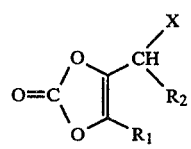

wherein R$_1$ represents a hydrogen atom, a methyl group, or an aryl group, R$_2$ represents a hydrogen atom, or may be taken together with $R_1$ to form a divalent carbon chain residue, and X represents Cl, Br or I.

2. The compound of claim 1 wherein $R_1$ is a methyl group and $R_2$ is a hydrogen atom.

3. The compound of claim 1 wherein $R_1$ and $R_2$ are hydrogen atoms.

4. The compound of claim 1 wherein $R_1$ is a phenyl group and $R_2$ is a hydrogen atom.

5. The compound of claim 1 wherein $R_1$ and $R_2$ together represent the group —(CH$_2$)$_3$ or —(CH$_2$)$_5$.

6. 4-Chloromethyl-5-methyl-1,3-dioxolen-2-one.
7. 4-Bromomethyl-5-methyl-1,3-dioxolen-2-one.
8. 4-Iodomethyl-5-methyl-1,3-dioxolen-2-one.
9. 4-Chloromethyl-5-phenyl-1,3-dioxolen-2-one.
10. 4-Bromomethyl-5-phenyl-1,3-dioxolen-2-one.
11. 4-Chloromethyl-1,3-dioxolen-2one.
12. 4-Bromomethyl-1,3-dioxolen-2-one.
13. 3-Chloro-1,2-carbonyldioxycyclohexene.
14. 3-Bromo-1,2-carbonyldioxycyclohexene.

* * * * *